(12) United States Patent
Fujikura et al.

(10) Patent No.: US 7,056,892 B2
(45) Date of Patent: Jun. 6, 2006

(54) GLUCOPYRANOSYLOXYPYRAZOLE DERIVATIVES, MEDICINAL COMPOSITIONS CONTAINING THE SAME AND INTERMEDIATES IN THE PRODUCTION THEREOF

(75) Inventors: Hideki Fujikura, Nagano (JP); Toshihiro Nishimura, Nagano (JP); Kenji Katsuno, Nagano (JP); Masahiro Hiratochi, Nagano (JP); Akira Iyobe, Nagano (JP); Minoru Fujioka, Nagano (JP); Masayuki Isaji, Nagano (JP)

(73) Assignee: Kissei Pharmaceutical Co., Ltd., Nagano (JP)

(*) Notice: Subject to any disclaimer, the term of this patent is extended or adjusted under 35 U.S.C. 154(b) by 44 days.

(21) Appl. No.: 11/189,832

(22) Filed: Jul. 27, 2005

(65) Prior Publication Data

US 2005/0261205 A1 Nov. 24, 2005

Related U.S. Application Data

(63) Continuation of application No. 10/759,138, filed on Jan. 20, 2004, which is a continuation of application No. 10/069,589, filed as application No. PCT/JP00/05678 on Aug. 24, 2000, now abandoned.

(30) Foreign Application Priority Data

Aug. 31, 1999 (JP) ................................ 11-246800

(51) Int. Cl.
*A61K 31/70* (2006.01)
*A61K 31/7042* (2006.01)
*A61K 31/415* (2006.01)
*C07H 17/00* (2006.01)

(52) U.S. Cl. ......................... 514/27; 514/25; 514/406; 514/407; 514/866; 514/909; 536/4.1; 548/373.1; 548/376.1; 548/366.1

(58) Field of Classification Search .................. 514/27, 514/25, 406, 407, 866, 909; 536/4.1; 548/373.1, 548/376.1, 366.1
See application file for complete search history.

(56) References Cited

U.S. PATENT DOCUMENTS

| 5,264,451 | A | 11/1993 | Kees |
| 5,274,111 | A | 12/1993 | Kees |
| 6,815,428 | B1 | 11/2004 | Ohsumi et al. |
| 2003/0087843 | A1 | 5/2003 | Washburn |
| 2005/0043249 | A1 | 2/2005 | Ohsumi et al. |

FOREIGN PATENT DOCUMENTS

WO     WO 03/020737 A1     3/2003

OTHER PUBLICATIONS

Brian E. Peerce, Molecular mechanism of two noncompetitive inhibitors of Na+glucose cotransporter; comparison of DCCD and PCMB; Am. J. Physiol., vol. 264, No. 2, Pt. 1, Pt. 1, pp. G300-305 (1993).
Borries Kubel: Einfache Synthese von 4-(Heteroarylmethyl)phenolen und deren Acylierung: Liebigs Ann. Chem., vol. 9, pp. 1392-1401(1980).
Kees et al., Journal of Medicinal Chemistry (1996), 39 (20), 3920-3928.

*Primary Examiner*—Samuel Barts
*Assistant Examiner*—Michael C. Henry
(74) *Attorney, Agent, or Firm*—Sughrue Mion, PLLC

(57) ABSTRACT

The present invention relates to glucopyranosyloxypyrazole derivatives represented by the general formula:

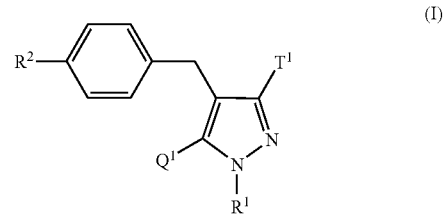

(I)

wherein $R^1$ represents a hydrogen atom or a lower alkyl group; one of $Q^1$ and $T^1$ represents a group represented by the general formula:

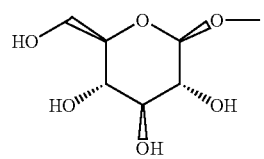

while the other represents a lower alkyl group or a halo (lower alkyl) group; and $R^2$ represents a hydrogen atom, a lower alkyl group, a lower alkoxy group, a lower alkylthio group, a halo(lower alkyl) group or a halogen atom, or pharmaceutically acceptable salts thereof, which have an inhibitory activity in human SGLT2 and are useful as agents for the prevention or treatment of diabetes, diabetic complications or obesity, and to pharmaceutical compositions comprising the same and intermediates thereof.

1 Claim, No Drawings

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: PCR primer 0702F

<400> SEQUENCE: 1
atggaggagc acacagaggc                                           20

<210> SEQ ID NO 2
<211> LENGTH: 20
<212> TYPE: DNA
<213> ORGANISM: Artificial Sequence
<220> FEATURE:
<223> OTHER INFORMATION: PCR primer 0712R

<400> SEQUENCE: 2
ggcatagaag ccccagagga                                           20

<210> SEQ ID NO 3
<211> LENGTH: 29
<212> TYPE: DNA

```
<213> ORGANISM: Artificial Sequence
<220> FEATURE:
<223> OTHER INFORMATION: PCR primer 0714F

<400> SEQUENCE: 3
aacctcgaga tggaggagca cacagaggc                              29

<210> SEQ ID NO 4
<211> LENGTH: 29
<212> TYPE: DNA
<213> ORGANISM: Artificial Sequence
<220> FEATURE:
<223> OTHER INFORMATION: PCR primer 0715R

<400> SEQUENCE: 4
aacaagcttg gcatagaagc cccagagga                              29

<210> SEQ ID NO 5
<211> LENGTH: 25
<212> TYPE: PRT
<213> ORGANISM: Artificial Sequence
<220> FEATURE:
<223> OTHER INFORMATION: Human SGLT2 carboxy-terminal tag

<400> SEQUENCE: 5

Lys Leu Gly Pro Glu Gln Lys Leu Ile Ser Glu Glu Asp Leu Asn Ser
 1               5                  10                  15

Ala Val Asp His His His His His His
            20                  25
```

GLUCOPYRANOSYLOXYPYRAZOLE DERIVATIVES, MEDICINAL COMPOSITIONS CONTAINING THE SAME AND INTERMEDIATES IN THE PRODUCTION THEREOF

This is a continuation of U.S. Ser. No. 10/759,138 filed Jan. 20, 2004, which is a continuation of U.S. Ser. No. 10/069,589 filed Feb. 27, 2002, now abandoned, which was an application under 35 U.S.C. 371 of PCT/JP00/05678 filed Aug. 24, 2000, claiming the benefit of JP 246800/1999 filed Aug. 31, 1999, the disclosures of which are hereby incorporated by reference.

TECHNICAL FIELD

The present invention relates to glucopyranosyloxypyrazole derivatives or pharmaceutically acceptable salts thereof, which are useful as medicaments, pharmaceutical compositions comprising the same and intermediates thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and insulin sensitivity enhancers have been employed as antidiabetic agents. However, biguanides and sulfonylureas show occasionally adverse effects such as lactic acidosis and hypoglysemia, respectively. In a case of using insulin sensitivity enhancers, adverse effects such as edema occasionally are observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510–1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397–404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents, which have a potent inhibitory activity in human SGLT2 and have a new mechanism, has been desired. Also, since such agents promote the excretion of excess glucose though the urine and consequently the glucose accumulation in the body is decreased, they are also expected to have a preventing or alleviating effect on obesity.

As compounds having pyrazole moiety, it is described that WAY-123783 increased an amount of excreted glucose in normal mice. However, its effects in human are not described at all (J. Med. Chem., Vol. 39, pp. 3920–3928 (1996)).

DISCLOSURE OF THE INVENTION

The present invention relates to a glucopyranosyloxypyrazole derivative represented by the general formula:

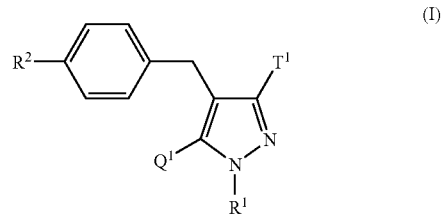

(I)

wherein $R^1$ represents a hydrogen atom or a lower alkyl group; one of $Q^1$ and $T^1$ represents a group represented by the formula:

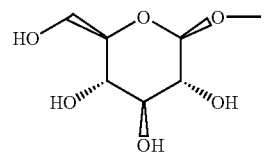

while the other represents a lower alkyl group or a halo (lower alkyl) group; and $R^2$ represents a hydrogen atom, a lower alkyl group, a lower alkoxy group, a lower alkylthio group, a halo(lower alkyl) group or a halogen atom, or a pharmaceutically acceptable salt thereof.

Also, the present invention relates to a pharmaceutical composition, which comprise as an active ingredient a glucopyranosyloxypyrazole derivative represented by the general formula:

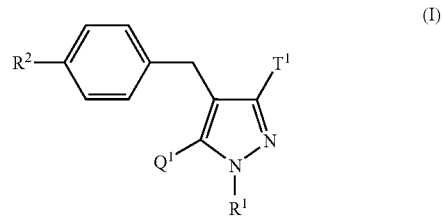

(I)

wherein $R^1$ represents a hydrogen atom or a lower alkyl group; one of $Q^1$ and $T^1$ represents a group represented by the formula:

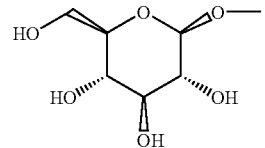

while the other represents a lower alkyl group or a halo (lower alkyl) group; and $R^2$ represents a hydrogen atom, a lower alkyl group, a lower alkoxy group, a lower alkylthio group, a halo(lower alkyl) group or a halogen atom, or a pharmaceutically acceptable salt thereof.

Furthermore, The present invention relates to a glucopyranosyloxypyrazole derivative represented by the general formula:

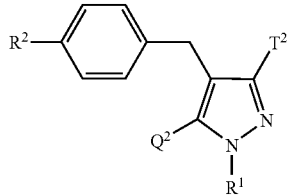

(VII)

wherein $R^1$ represents a hydrogen atom or a lower alkyl group; one of $Q^2$ and $T^2$ represents a 2,3,4,6-tetra-O-acetyl-β-D-glucopyranosyloxy group, while the other represents a lower alkyl group or a halo(lower alkyl) group; and $R^2$ represents a hydrogen atom, a lower alkyl group, a lower alkoxy group, a lower alkylthio group, a halo(lower alkyl) group or a halogen atom, or a salt thereof, and to a benzylpyrazole derivative represented by the general formula:

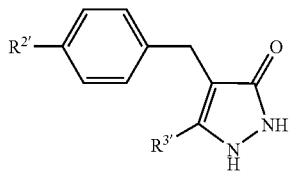

(Va)

wherein $R^{2'}$ represents a lower alkyl group, a lower alkoxy group, a lower alkylthio group, a halo(lower alkyl) group or a halogen atom; and $R^{3'}$ represents a lower alkyl group, or a salt thereof.

BEST MODE FOR CARRYING OUT THE INVENTION

The present inventors have studied earnestly to find compounds having an inhibitory activity in human SGLT2. As a result, it was found that glucopyranosyloxypyrazole derivatives represented by the above general formula (I) exhibit an excellent inhibitory activity in human SGLT2 as mentioned below, thereby forming the basis of the present invention.

This is, the present invention relates to a glucopyranosyloxypyrazole derivative represented by the general formula:

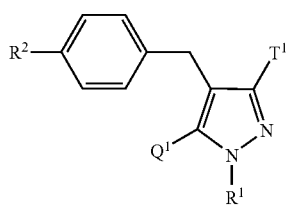

(I)

wherein $R^1$ represents a hydrogen atom or a lower alkyl group; one of $Q^1$ and $T^1$ represents a group represented by the formula:

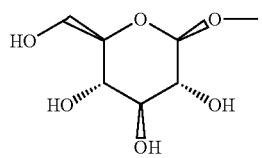

while the other represents a lower alkyl group or a halo (lower alkyl) group; and $R^2$ represents a hydrogen atom, a lower alkyl group, a lower alkoxy group, a lower alkylthio group, a halo(lower alkyl) group or a halogen atom, or a pharmaceutically acceptable salt thereof, a pharmaceutical composition comprising the same and an intermediate thereof.

In the compounds represented by the above general formula (I), the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "halogen atom" means a fluorine atom, a chlorine atom, a bromine atom or an iodine atom; and the term "halo(lower alkyl) group" means the above lower alkyl group substituted by different or same 1 to 3 halogen atoms as defined above.

In the substituent $R^1$, a hydrogen atom or a straight-chained or branched alkyl group having 1 to 3 carbon atoms are preferable; and a hydrogen atom, an ethyl group, a propyl group or an isopropyl group are more preferable. In the substituent $R^2$, a straight-chained or branched alkyl group having 1 to 4 carbon atoms, a straight-chained or branched alkoxy group having 1 to 3 carbon atoms, or a straight-chained or branched alkylthio group having 1 to 3 carbon atoms are preferable; and an ethyl group, an ethoxy group, an isopropoxy group or a methylthio group are more preferable. In the substituents $Q^1$ and $T^1$, it is preferable that either of them is a straight-chained or branched alkyl group having 1 to 3 carbon atoms, and it is more preferable that either of them is a methyl group.

For example, the compounds represented by the above general formula (I) of the present invention can be prepared according to the following procedure:

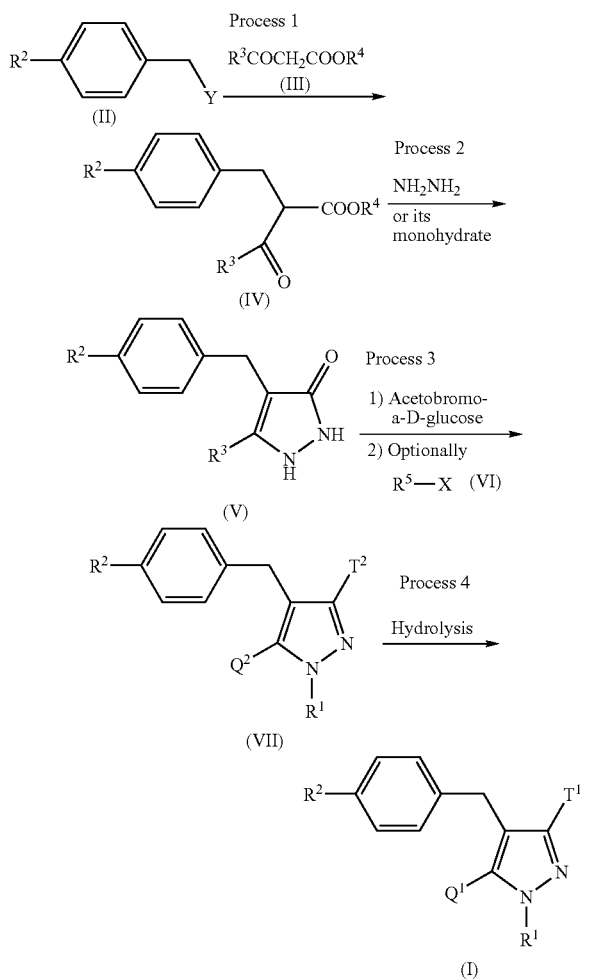

wherein X and Y represent a leaving group such as a halogen atom, a mesyloxy group or a tosyloxy group; $R^3$ represents a lower alkyl group or a halo(lower alkyl) group; $R^4$ represents a methyl group or an ethyl group; $R^5$ represents a lower alkyl group; one of $Q^2$ and $T^2$ represents a 2,3,4,6-tetra-O-acetyl-β-D-glucopyranosyloxy group, while the other represents a lower alkyl group or a halo(lower alkyl) group; and $R^1$, $R^2$, $Q^1$ and $T^1$ have the same meanings as defined above.

Process 1

A compound represented by the above general formula (IV) can be prepared by condensing a benzyl derivative represented by the above general formula (II) with a ketoacetate represented by the above general formula (III) in the presence of a base such as sodium hydride or potassium tert-butoxide in an inert solvent. As the inert solvent used in the reaction, 1,2-dimethoxyethane, tetrahydrofuran, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 2

A pyrazolone derivative represented by the above general formula (V) can be prepared by condensing a compound represented by the above general formula (IV) with hydrazine or hydrazine monohydrate in an inert solvent. As the inert solvent used in the reaction, toluene, tetrahydrofuran, chloroform, a mixed solvent thereof and the like can be illustrated. The reaction temperature is usually from room temperature to reflux temperature, and the reaction time is usually from 1 hour to 1 day, varying based on a used starting material, solvent and reaction temperature. The obtained pyrazolone derivative represented by the above general formula (V) can be also used in process 3 after converting into a salt thereof in usual way.

Process 3

(1) In case of pyrazolone derivatives represented by the above general formula (V) wherein $R^3$ is a lower alkyl group, a corresponding compound represented by the above general formula (VII) can be prepared by subjecting a corresponding pyrazolone derivative represented by the above general formula (V) to glycosidation using acetobromo-α-D-glucose in the presence of a base such as silver carbonate in an inert solvent, and subjecting the resulting compound to N-alkylation using an alkylating agent represented by the above general formula (VI) in the presence of a base such as pottasium carbonate in an inert solvent as occasion demands. As the solvent used in the glycosidation reaction, tetrohydrofuran and the like can be illustrated. The reaction temperature is usually from room temperature to reflux temperature, and the reaction time is usually from 1 hour to 1 day, varying based on a used starting material, solvent and reaction temperature. As the solvent used in the N-alkylation reaction, acetonitrile, N,N-dimethylformamide, tetrohydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature.

(2) In case of pyrazolone derivatives represented by the above general formula (V) wherein $R^3$ is a halo(lower alkyl) group, a corresponding compound represented by the above general formula (VII) can be prepared by subjecting a corresponding pyrazolone derivative represented by the above general formula (V) to glycosidation using acetobromo-α-D-glucose in the presence of a base such as potassium carbonate in an inert solvent, and subjecting the resulting compound to N-alkylation using an alkylating agent represented by the above general formula (VI) in the presence of a base such as pottasium carbonate in an inert solvent as occasion demands. As the solvent used in the glycosidation reaction, acetonitrile, tetrahydrofuran and the like can be illustrated. The reaction temperature is usually from room temperature to reflux temperature, and the reaction time is usually from 1 hour to 1 day, varying based on a used starting material, solvent and reaction temperature. As the solvent used in the N-alkylation reaction, acetonitrile, N,N-dimethylformamide, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature.

The obtained compounds represented by the above general formula (VII) can be also used in process 4 after converting into a salt thereof in usual way.

Process 4

A compound (I) of the present invention can be prepared by subjecting a compound represented by the above general formula (VII) to alkaline hydrolysis. As the solvent used in the reaction, methanol, ethanol, tetrahydrofuran, water, a mixed solvent thereof and the like can be illustrated, and as the base used, sodium hydroxide, sodium ethoxide and the like can be illustrated. The reaction temperature is usually from 0° C. to room temperature, and the reaction time is usually from 30 minutes to 6 hours, varying based on a used starting material, solvent and reaction temperature.

Of the compounds represented by the above general formula (I), compounds wherein the substituent $R^1$ is a lower alkyl group can be prepared according to the following procedure:

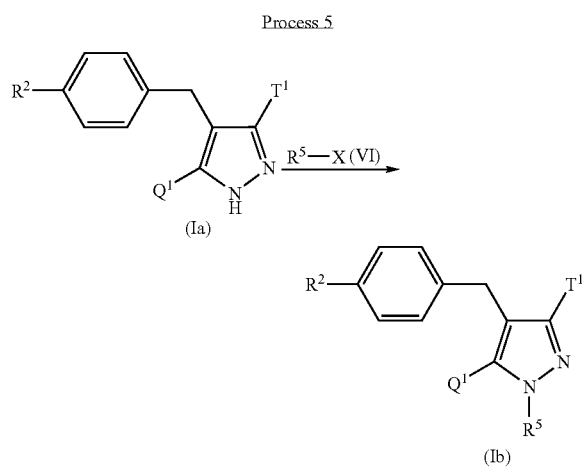

wherein $Q^1$, $R^2$, $R^5$, $T^1$ and X have the same meanings as defined above.

Process 5

A compound represented by the above general formula (Ib) of the present invention can be prepared by subjecting a compound represented by the above general formula (Ia) of the present invention to N-alkylation using an N-alkylating agent represented by the above general formula (VI) in the presence of a base such as potassium carbonate or cesium carbonate, and occasionally a catalytic amount of sodium iodide in an inert solvent. As the inert solvent used in the reaction, N,N-dimethylformamide, dimethoxyethane, dimethyl sulfoxide, tetrahydrofuran, ethanol, a mixed solvent thereof and the like can be illustrated. The reaction temperature is usually from room temperature to reflux temperature, and the reaction time is usually from 10 minutes to 1 day, varying based on a used starting material, solvent and reaction temperature.

The compounds represented by the above general formula (VII) and salts thereof which are used in the aforementioned production process are useful compounds as intermediates of compounds represented by the above general formula (I) of the present invention. In the compounds represented by the above general formula (VII) as well as the compounds represented by the above general formula (I) of the present invention, it is preferable that either of the substituents $Q^2$ and $T^2$ is a straight-chained or branched alkyl group having 1 to 3 carbon atoms, and it is more preferable that either of them is a methyl group.

In the compound represented by the above general formula (V) as starting materials, there are the following three tautomers, varying based on the change of reaction conditions:

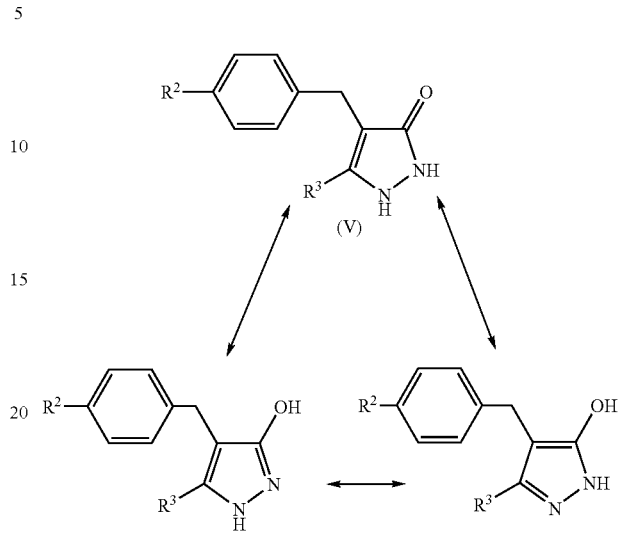

wherein $R^2$ and $R^3$ have the same meanings as defined above. The compounds represented by the above general formula (V) and salts thereof which are used in the aforementioned production process are useful compounds as intermediates of compounds represented by the above general formula (I) of the present invention. In the compounds represented by the above general formula (V) as well as the compounds represented by the above general formula (I) of the present invention, it is preferable that the substituent $R^3$ is a straight-chained or branched alkyl group having 1 to 3 carbon atoms, and it is more preferable that the substituent $R^3$ is a methyl group.

The compounds represented by the above general formula (I) of the present invention obtained by the above production processes can be isolated and purified by conventional separation means such as fractional recrystallization, purification using chromatography and solvent extraction.

The glucopyranosyloxypyrazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, and salts with inorganic bases such as a sodium salt, a potassium salt and the like.

The compounds represented by the above general formula (I) of the present invention include their their solvates with pharmaceutically acceptable solvents such as ethanol and water.

The compounds represented by the above general formula (I) of the present invention have an excellent inhibitory activity in human SGLT2 and are extremely useful as agents for the prevention or treatment of diabetes, diabetic complications, obesity and the like. For example, in the following assay for inhibitory effect on human SGLT2 activity, the compounds of the present invention exerted a potent inhibitory activity in human SGLT2. On the other hand, since WAY-123783 has an extremely weak inhibitory activity in human SGLT2, it can not be expected to exert an enough effect as a human SGLT2 inhibitor.

When the pharmaceutical compositions of the present invention are employed in the practical treatment, various dosage forms are used depending on their uses. As examples of the dosage forms, powders, granules, fine granules, dry sirups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with the conventional manner.

When the pharmaceutical compositions of the present invention are employed in the practical treatment, the dosage of a compound represented by the above general formula (I) or a pharmaceutically acceptable salt thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably.

EXAMPLES

The present invention is further illustrated in more detail by way of the following Reference Examples, Examples and Test Examples. However, the present invention is not limited thereto.

Example 1

1,2-Dihydro-4-[(4-isopropoxyphenyl)methyl]-5-methyl-3H-pyrazol-3-one

To a solution of 4-isopropoxybenzylalcohol (0.34 g) in tetrahydrofuran (6 mL) were added triethylamine (0.28 mL) and methanesulfonyl chloride (0.16 mL), and the mixture was stirred at room temperature for 30 minutes. The resulting insoluble material was removed by filtration. The obtained solution of 4-isopropoxybenzyl methanesulfonate in tetrahydrofuran was added to a suspension of sodium hydride (60%, 81 mg) and methyl acetoacetate (0.20 mL) in 1,2-dimethoxyethane (10 mL), and the mixture was stirred at 80° C. overnight. The reaction mixture was poured into a saturated aqueous sodium hydrogen carbonate solution, and the resulting mixture was extracted with diethyl ether. The organic layer was washed with brine and dried over anhydrous magnesium sulfate. The solvent was removed under reduced pressure, and the residue was dissolved in toluene (5 mL). Anhydrous hydrazine (0.19 mL) was added to the solution, and the mixture was stirred at 80° C. overnight. The solvent was removed under reduced pressure, and the residue was purified by column chromatography on silica gel (eluent: dichloromethane/methanol=10/1) to give 1,2-dihydro-4-[(4-isopropoxyphenyl)methyl]-5-methyl-3H-pyrazol-3-one (95 mg).

$^1$H-NMR (500 MHz, DMSO-$d_6$) δ ppm: 1.22 (6H, d, J=6.0 Hz), 1.99 (3H, s), 3.45 (2H, s), 4.40–4.60 (1H, m), 6.65–6.80 (2H, m), 6.95–7.10 (2H, m)

Example 2

1,2-Dihydro-5-methyl-4-[(4-propylphenyl)methyl]-3H-pyrazol-3-one

The title compound was prepared in a similar manner to that described in Example 1 using 4-propylbenzyl alcohol instead of 4-isopropoxybenzyl alcohol.

$^1$H-NMR (500 MHz, DMSO-$d_6$) δ ppm: 0.75–0.95 (3H, m), 1.45–1.65 (2H, m), 1.99 (3H, s), 2.40–2.55 (2H, m), 3.32 (2H, s), 6.95–7.10 (4H, m)

Example 3

1,2-Dihydro-4-[(4-isobutylphenyl)methyl]-5-methyl-3H-pyrazol-3-one

The title compound was prepared in a similar manner to that described in Example 1 using 4-isobutylbenzyl alcohol instead of 4-isopropoxybenzyl alcohol.

$^1$H-NMR (500 MHz, DMSO-$d_6$) δ ppm: 0.83 (6H, d, J=6.6 Hz), 1.70–1.85 (1H, m), 1.99 (3H, s), 2.30–2.45 (2H, m), 3.50 (2H, s), 6.90–7.10 (4H, m)

Example 4

1,2-Dihydro-5-methyl-4-[(4-propoxyphenyl)methyl]-3H-pyrazol-3-one

The title compound was prepared in a similar manner to that described in Example 1 using 4-propoxybenzyl alcohol instead of 4-isopropoxybenzyl alcohol.

$^1$H-NMR (500 MHz, DMSO-$d_6$) δ ppm: 0.95 (3H, t, J=7.4 Hz), 1.60–1.75 (2H, m), 1.98 (3H, s), 3.46 (2H, s), 3.75–3.90 (2H, m), 6.70–6.85 (2H, m), 6.95–7.10 (2H, m)

Example 5

4-[(4-Ethoxyphenyl)methyl]-1,2-dihydro-5-methyl-3H-pyrazol-3-one

The title compound was prepared in a similar manner to that described in Example 1 using 4-ethoxybenzyl alcohol instead of 4-isopropoxybenzyl alcohol.

$^1$H-NMR (500 MHz, DMSO-$d_6$) δ ppm: 1.20–1.35 (3H, m), 1.98 (3H, s), 3.46 (2H, s), 3.85–4.05 (2H, m), 6.70–6.85 (2H, m), 6.95–7.10 (2H, m)

Example 6

1,2-Dihydro-5-methyl-4-[(4-trifluoromethylphenyl)methyl]-3H-pyrazol-3-one

The title compound was prepared in a similar manner to that described in Example 1 using 4-trifluoromethylbenzyl alcohol instead of 4-isopropoxybenzyl alcohol.

$^1$H-NMR (500 MHz, DMSO-$d_6$) δ ppm: 2.02 (3H, s), 3.64 (2H, s), 7.30–7.45 (2H, m), 7.55–7.70 (2H, m)

Example 7

4-[(4-tert-Butylphenyl)methyl]-1,2-dihydro-5-methyl-3H-pyrazol-3-one

The title compound was prepared in a similar manner to that described in Example 1 using 4-tert-butylbenzyl alcohol instead of 4-isopropoxybenzyl alcohol.

$^1$H-NMR (500 MHz, DMSO-$d_6$) δ ppm: 1.24 (9H, s), 2.01 (3H, s), 3.49 (2H, s), 7.00–7.15 (2H, m), 7.15–7.30 (2H, m)

Example 8

4-[(4-Butoxyphenyl)methyl]-1,2-dihydro-5-methyl-3H-pyrazol-3-one

The title compound was prepared in a similar manner to that described in Example 1 using 4-butoxybenzyl alcohol instead of 4-isopropoxybenzyl alcohol.

$^1$H-NMR (500 MHz, DMSO-$d_6$) δ ppm: 0.91 (3H, t, J=7.4 Hz), 1.30–1.50 (2H, m), 1.55–1.75 (2H, m), 1.98 (3H, s), 3.46 (2H, s), 3.80–3.95 (2H, m), 6.70–6.85 (2H, m), 6.95–7.10 (2H, m)

Example 9

1,2-Dihydro-5-methyl-4-[(4-methylthiophenyl)methyl]-3H-pyrazol-3-one

The title compound was prepared in a similar manner to that described in Example 1 using 4-(methylthio)benzyl alcohol instead of 4-isopropoxybenzyl alcohol.

$^1$H-NMR (500 MHz, DMSO-$d_6$) δ ppm: 1.99 (3H, s), 2.42 (3H, s), 3.50 (2H, s), 7.05–7.20 (4H, m)

Example 10

5-Ethyl-1,2-dihydro-4-[(4-methylthiophenyl)methyl]-3H-pyrazol-3-one

The title compound was prepared in a similar manner to that described in Example 1 using 4-(methylthio)benzyl alcohol instead of 4-isopropoxybenzyl alcohol and using methyl 3-oxopentanoate instead of methyl acetoacetate.

$^1$H-NMR (500 MHz, DMSO-$d_6$) δ ppm: 1.02 (3H, t, J=7.6 Hz), 2.39 (2H, q, J=7.6 Hz), 2.42 (3H, s), 3.51 (2H, s), 7.05–7.20 (4H, m)

Example 11

1,2-Dihydro-4-[(4-isopropylphenyl)methyl]-5-methyl-3H-pyrazol-3-one

To a suspension of sodium hydride (60%, 40 mg) in 1,2-dimethoxyethane (1 mL) were added methyl acetoacetate (0.11 mL), 4-isopropylbenzyl chloride (0.17 g) and a catalytic amount of sodium iodide, and the mixture was stirred at 80° C. overnight. The reaction mixture was poured into a saturated aqueous sodium hydrogen carbonate solution, and the mixture was extracted with diethyl ether. The organic layer was washed with brine and dried over anhydrous magnesium sulfate. The solvent was removed under reduced pressure, and the residue was dissolved in toluene (1 mL). Anhydrous hydrazine (0.094 mL) was added to the solution, and the mixture was stirred at 80° C. overnight. The solvent was removed under reduced pressure, and the residue was purified by column chromatography on silica gel (eluent: dichloromethane/methanol=10/1) to give 1,2-dihydro-4-[(4-isopropylphenyl)methyl]-5-methyl-3H-pyrazol-3-one (0.12 g).

$^1$H-NMR (500 MHz, DMSO-$d_6$) δ ppm: 1.16 (6H, d, J=6.9 Hz), 2.01 (3H, s), 2.70–2.90 (1H, m), 3.49 (2H, s), 6.95–7.20 (4H, m)

Example 12

4-[(4-Ethylphenyl)methyl]-1,2-dihydro-5-methyl-3H-pyrazol-3-one

The title compound was prepared in a similar manner to that described in Example 11 using 4-ethylbenzyl chloride instead of 4-isopropylbenzyl chloride.

$^1$H-NMR (500 MHz, DMSO-$d_6$) δ ppm: 1.13 (3H, t, J=7.6 Hz), 2.00 (3H, s), 2.45–2.60 (2H, m), 3.49 (2H, s), 7.00–7.15 (4H, m)

Example 13

1,2-Dihydro-5-methyl-4-[(4-methylphenyl)methyl]-3H-pyrazol-3-one

The title compound was prepared in a similar manner to that described in Example 11 using 4-methylbenzyl bromide instead of 4-isopropylbenzyl chloride.

$^1$H-NMR (500 MHz, DMSO-$d_6$) δ ppm: 1.98 (3H, s), 2.23 (3H, s), 3.48 (2H, s), 6.95–7.10 (4H, m)

Reference Example 1

4-Benzyl-1,2-dihydro-5-trifluoromethyl-3H-pyrazol-3-one

The title compound was prepared in a similar manner to that described in Example 11 using ethyl trifluoroacetoacetate instead of methyl acetoacetate and using benzyl bromide instead of 4-isopropylbenzyl chloride.

$^1$H-NMR (500 MHz, DMSO-$d_6$) δ ppm: 3.73 (2H, s), 7.05–7.35 (5H, m), 12.50–13.10 (1H, brs)

Example 14

1,2-Dihydro-4-[(4-methoxyphenyl)methyl]-5-methyl-3H-pyrazol-3-one

The title compound was prepared in a similar manner to that described in Example 11 using 4-methoxybenzyl bromide instead of 4-isopropylbenzyl chloride.

$^1$H-NMR (500 MHz, DMSO-$d_6$) δ ppm: 1.99 (3H, s), 3.47 (2H, s), 3.69 (3H, s), 6.75–6.85 (2H, m), 7.00–7.10 (2H, m), 8.70–11.70 (2H, br)

Reference Example 2

4-Benzyl-1,2-dihydro-5-methyl-3H-pyrazol-3-one

The title compound was prepared in a similar manner to that described in Example 11 using benzyl bromide instead of 4-isopropylbenzyl chloride.

$^1$H-NMR (500 MHz, DMSO-$d_6$) δ ppm: 2.00 (3H, s), 3.54 (2H, s), 7.05–7.30 (5H, s)

Example 15

4-[(4-Isopropoxyphenyl)methyl]-5-methyl-3-(2,3,4,6-tetra-O-acetyl-β-D-glucopyranosyloxy)-1H-pyrazole To a suspension of 1,2-dihydro-4-[(4-isopropoxyphenyl)methyl]-5-methyl-3H-pyrazol-3-one (46 mg), acetobromo-α-D-glucose (99 mg) and 4A molecular sieves in tetrahydrofuran (3 mL) was added silver carbonate (66 mg), and the mixture was stirred under shading the light at 65° C. overnight. The reaction mixture was purified by column chromatography on aminopropyl silica gel (eluent: tetrahydrofuran). Further purification by preparative thin layer chromatography on silica gel (developing solvent: ethyl acetate/hexane=2/1) afforded 4-[(4-isopropoxyphenyl)methyl]-5-methyl-3-(2,3,4,6-tetra-O-acetyl-β-D-glucopyranosyloxy)-1H-pyrazole (42 mg).

$^1$H-NMR (500 MHz, CDCl$_3$) δ ppm: 1.25–1.35 (6H, m), 1.88 (3H, s), 2.01 (3H, s), 2.03 (3H, s), 2.05 (3H, s), 2.10 (3H, s), 3.45–3.65 (2H, m), 3.80–3.90 (1H, m), 4.13 (1H, dd, J=2.3, 12.4 Hz), 4.31 (1H, dd, J=4.0, 12.4 Hz), 4.40–4.55 (1H, m), 5.15–5.35 (3H, m), 5.50–5.60 (1H, m), 6.70–6.80 (2H, m), 6.95–7.05 (2H, m)

Example 16

5-Methyl-4-[(4-propylphenyl)methyl]-3-(2,3,4,6-tetra-O-acetyl-β-D-glucopyranosyloxy)-1H-pyrazole The title compound was prepared in a similar manner to that described in Example 15 using 1,2-dihydro-5-methyl-4-[(4-propylphenyl)methyl]-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 0.91 (3H, t, J=7.3 Hz), 1.50–1.65 (2H, m), 1.86 (3H, s), 2.01 (3H, s), 2.03 (3H, s), 2.05 (3H, s), 2.10 (3H, s), 2.45–2.55 (2H, m), 3.55 (1H, d, J=15.8 Hz), 3.63 (1H, d, J=15.8 Hz), 3.80–3.90 (1H, m), 4.13 (1H, dd, J=2.3, 12.4 Hz), 4.30 (1H, dd, J=3.9, 12.4 Hz), 5.15–5.35 (3H, m), 5.50–5.60 (1H, m), 7.00–7.20 (4H, m)

Example 17

4-[(4-Isobutylphenyl)methyl]-5-methyl-3-(2,3,4,6-tetra-O-acetyl-β-D-glucopyranosyloxy)-1H-pyrazole The title compound was prepared in a similar manner to that described in Example 15 using 1,2-dihydro-4-[(4-isobutylphenyl)methyl]-5-methyl-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 0.87 (6H, d, J=6.6 Hz), 1.70–1.85 (1H, m), 1.87 (3H, s), 2.01 (3H, s), 2.03 (3H, s), 2.06 (3H, s), 2.10 (3H, s), 2.40 (2H, d, J=7.2 Hz), 3.56 (1H, d, J=15.8 Hz), 3.63 (1H, d, J=15.8 Hz), 3.80–3.90 (1H, m), 4.14 (1H, dd, J=2.3, 12.4 Hz), 4.31 (1H, dd, J=4.0, 12.4 Hz), 5.15–5.35 (3H, m), 5.50–5.60 (1H, m), 6.95–7.10 (4H, m)

Example 18

5-Methyl-4-[(4-propoxyphenyl)methyl]-3-(2,3,4,6-tetra-O-acetyl-β-D-glucopyranosyloxy)-1H-pyrazole The title compound was prepared in a similar manner to that described in Example 15 using 1,2-dihydro-5-methyl-4-[(4-propoxyphenyl)methyl]-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.01 (3H, t, J=7.4 Hz), 1.70–1.85 (2H, m), 1.89 (3H, s), 2.01 (3H, s), 2.03 (3H, s), 2.06 (3H, s), 2.10 (3H, s), 3.53 (1H, d, J=15.7 Hz), 3.59 (1H, d, J=15.7 Hz), 3.80–3.95 (3H, m), 4.14 (1H, dd, J=2.3, 12.4 Hz), 4.31 (1H, dd, J=4.0, 12.4 Hz), 5.15–5.35 (3H, m), 5.50–5.60 (1H, m), 6.70–6.80 (2H, m), 6.95–7.10 (2H, m)

Example 19

4-[(4-Ethoxyphenyl)methyl]-5-methyl-3-(2,3,4,6-tetra-O-acetyl-β-D-glucopyranosyloxy)-1H-pyrazole The title compound was prepared in a similar manner to that described in Example 15 using 4-[(4-ethoxyphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.38 (3H, t, J=7.0 Hz), 1.89 (3H, s), 2.01 (3H, s), 2.03 (3H, s), 2.06 (3H, s), 2.10 (3H, s), 3.53 (1H, d, J=15.8 Hz), 3.59 (1H, d, J=15.8 Hz), 3.80–3.90 (1H, m), 3.98 (2H, q, J=7.0 Hz), 4.13 (1H, dd, J=2.3, 12.4 Hz), 4.31 (1H, dd, J=4.0, 12.4), 5.15–5.30 (3H, m), 5.50–5.60 (1H, m), 6.70–6.80 (2H, m), 6.95–7.10 (2H, m)

Example 20

5-Methyl-3-(2,3,4,6-tetra-O-acetyl-β-D-glucopyranosyloxy)-4-[(4-trifluoromethylphenyl)methyl]-1H-pyrazole The title compound was prepared in a similar manner to that described in Example 15 using 1,2-dihydro-5-methyl-4-[(4-trifluoromethylphenyl)methyl]-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.85 (3H, s), 2.01 (3H, s), 2.03 (3H, s), 2.06 (3H, s), 2.14 (3H, s), 3.65 (1H, d, J=15.9 Hz), 3.71 (1H, d, J=15.9 Hz), 3.80–3.90 (1H, m), 4.14 (1H, dd, J=2.4, 12.4 Hz), 4.31 (1H, dd, J=4.0, 12.4 Hz), 5.15–5.40 (3H, m), 5.55–5.65 (1H, m), 7.20–7.30 (2H, m), 7.45–7.55 (2H, m)

Example 21

4-[(4-tert-Butylphenyl)methyl]-5-methyl-3-(2,3,4,6-tetra-O-acetyl-β-D-glucopyranosyloxy)-1H-pyrazole The title compound was prepared in a similar manner to that described in Example 15 using 4-[(4-tert-butylphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.27 (9H, s), 1.84 (3H, s), 2.01 (3H, s), 2.03 (3H, s), 2.06 (3H, s), 2.14 (3H, s), 3.56 (1H, d, J=15.8 Hz), 3.64 (1H, d, J=15.8 Hz), 3.80–3.90 (1H, m), 4.13 (1H, dd, J=2.3, 12.4 Hz), 4.31 (1H, dd, J=4.0, 12.4 Hz), 5.15–5.30 (3H, m), 5.50–5.60 (1H, m), 7.00–7.10 (2H, m), 7.20–7.30 (2H, m)

Example 22

4-[(4-Butoxyphenyl)methyl]-5-methyl-3-(2,3,4,6-tetra-O-acetyl-β-D-glucopyranosyloxy)-1H-pyrazole The title compound was prepared in a similar manner to that described in Example 15 using 4-[(4-butoxyphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 0.96 (3H, t, J=7.4 Hz), 1.40–1.55 (2H, m), 1.65–1.80 (2H, m), 1.88 (3H, s), 2.01 (3H, s), 2.03 (3H, s), 2.06 (3H, s), 2.10 (3H, s), 3.52 (1H, d, J=15.8 Hz), 3.59 (1H, d, J=15.8 Hz), 3.80–3.90 (1H, m), 3.91 (2H, t, J=6.5 Hz), 4.13 (1H, dd, J=2.3, 12.4 Hz), 4.31 (1H, dd, J=4.0, 12.4 Hz), 5.15–5.30 (3H, m), 5.50–5.60 (1H, m), 6.70–6.80 (2H, m), 6.95–7.10 (2H, m)

Example 23

5-Methyl-4-[(4-methylthiophenyl)methyl]-3-(2,3,4,6-tetra-O-acetyl-β-D-glucopyranosyloxy)-1H-pyrazole The title compound was prepared in a similar manner to that described in Example 15 using 1,2-dihydro-5-methyl-4-[(4-methylthiophenyl)methyl]-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.88 (3H, s), 2.01 (3H, s), 2.03 (3H, s), 2.07 (3H, s), 2.12 (3H, s), 2.44 (3H, s), 3.50–3.65 (2H, m), 3.80–3.90 (1H, m), 4.13 (1H, dd, J=2.4, 12.4 Hz), 4.31 (1H, dd, J=4.1, 12.4 Hz), 5.15–5.30 (3H, m), 5.55–5.65 (1H, m), 7.00–7.10 (2H, m), 7.10–7.20 (2H, m), 8.65–8.85 (1H, brs)

Example 24

5-Ethyl-4-[(4-methylthiophenyl)methyl]-3-(2,3,4,6-tetra-O-acetyl-β-D-glucopyranosyloxy)-1H-pyrazole The title compound was prepared in a similar manner to that described in Example 15 using 5-ethyl-1,2-dihydro-4-[(4-methylthiophenyl)methyl]-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.13 (3H, t, J=7.6 Hz), 1.88 (3H, s), 2.01 (3H, s), 2.03 (3H, s), 2.06 (3H, s), 2.44 (3H, s), 2.45–2.55 (2H, m), 3.50–3.70 (2H, m), 3.80–3.90 (1H, m), 4.05–4.20 (1H, m), 4.31 (1H, dd, J=4.0, 12.4 Hz), 5.15–5.35 (3H, m), 5.55–5.65 (1H, m), 7.00–7.10 (2H, m), 7.10–7.20 (2H, m), 8.80–9.20 (1H, brs)

Example 25

4-[(4-Isopropylphenyl)methyl]-5-methyl-3-(2,3,4,6-tetra-O-acetyl-β-D-glucopyranosyloxy)-1H-pyrazole The title compound was prepared in a similar manner to that described in Example 15 using 1,2-dihydro-4-[(4-isopropylphenyl)methyl]-5-methyl-3H-pyrazol-3-one instead of 1,2-dihydro-4-[(4-isopropoxyphenyl)methyl]-5-methyl-3H-pyrazol-3-one.

$^1$H-NMR (500 MHz, CDCl$_3$) δ ppm: 1.20 (6H, d, J=6.9 Hz), 1.85 (3H, s), 2.01 (3H, s), 2.03 (3H, s), 2.06 (3H, s), 2.13 (3H, s), 2.75–2.90 (1H, m), 3.56 (1H, d, J=15.8 Hz), 3.63 (1H, d, J=15.8 Hz), 3.80–3.90 (1H, m), 4.05–4.20 (1H, m), 4.31 (1H, dd, J=4.0, 12.4 Hz), 5.15–5.35 (3H, m), 5.50–5.60 (1H, m), 7.00–7.15 (4H, m), 8.70–9.30 (1H, brs)

Example 26

4-[(4-Methylthiophenyl)methyl]-3-(2,3,4,6-tetra-O-acetyl-β-D-glucopyranosyloxy)-5-trifluoromethyl-1H-pyrazole To a solution of 1,2-dihydro-4-[(4-methylthiophenyl)methyl]-5-trifluoromethyl-3H-pyrazol-3-one (2.0 g) in acetonitrile (100 mL) were added acetobromo-α-D-glucose (3.1 g) and potassium carbonate (1.1 g), and the mixture was stirred at room temperature overnight. Water was added to the reaction mixture, and the resulting mixture was extracted with ethyl acetate. The organic layer was washed with a saturated aqueous sodium hydrogen carbonate solution and brine, and dried over anhydrous magnesium sulfate. The solvent was removed under reduced pressure, and the residue was purified by column chromatography on silica gel (eluent: hexane/ethyl acetate=1/1) to give 4-[(4-methylthiophenyl)methyl]-3-(2,3,4,6-tetra-O-acetyl-β-D-glucopyranosyloxy)-5-trifluoromethyl-1H-pyrazole (2.0 g).

$^1$H-NMR (500 MHz, CDCl$_3$) δ ppm: 1.91 (3H, s), 2.03 (3H, s), 2.04 (3H, s), 2.09 (3H, s), 2.45 (3H, s), 3.73 (2H, s), 3.75–3.90 (1H, m), 4.15–4.35 (2H, m), 5.15–5.65 (4H, m), 7.00–7.20 (4H, m)

Example 27

4-Benzyl-3-(2,3,4,6-tetra-O-acetyl-β-D-glucopyranosyloxy)-5-trifluoromethyl-1H-pyrazole The title compound was prepared in a similar manner to that described in Example 26 using 4-benzyl-1,2-dihydro-5-trifluoromethyl-3H-pyrazol-3-one instead of 1,2-dihydro-4-[(4-methylthiophenyl)methyl]-5-trifluoromethyl-3H-pyrazol-3-one.

$^1$H-NMR (500 MHz, CDCl$_3$) δ ppm: 1.89 (3H, s), 2.02 (3H, s), 2.04 (3H, s), 2.08 (3H, s), 3.70–3.90 (3H, m), 4.15–4.30 (2H, m), 5.10–5.50 (4H, m), 7.10–7.30 (5H, m)

Example 28

4-[(4-Methoxyphenyl)methyl]-3-(2,3,4,6-tetra-O-acetyl-β-D-glucopyranosyloxy)-5-trifluoromethyl-1H-pyrazole The title compound was prepared in a similar manner to that described in Example 26 using 1,2-dihydro-4-[(4-methoxyphenyl)methyl]-5-trifluoromethyl-3H-pyrazol-3-one instead of 1,2-dihydro-4-[(4-methylthiophenyl)methyl]-5-trifluoromethyl-3H-pyrazol-3-one.

$^1$H-NMR (400 MHz, CDCl$_3$) δ ppm: 1.93 (3H, s), 2.03 (3H, s), 2.05 (3H, s), 2.09 (3H, s), 3.65–3.75 (2H, m), 3.77 (3H, s), 3.75–3.90 (1H, m), 4.15–4.35 (2H, m), 5.10–5.45 (4H, m), 6.75–6.85 (2H, m), 7.00–7.15 (2H, m)

Example 29

4-[(4-Methoxyphenyl)methyl]-5-methyl-3-(2,3,4,6-tetra-O-acetyl-β-D-glucopyranosyloxy)-1H-pyrazole The title compound was prepared in a similar manner to that described in Example 15 using 1,2-dihydro-4-[(4-methoxyphenyl)methyl]-5-methyl-3H-pyrazol-3-one instead of 1,2-dihydro-4-[(4-isopropoxyphenyl)methyl]-5-methyl-3H-pyrazol-3-one.

¹H-NMR (400 MHz, CDCl₃) δ ppm: 1.89 (3H, s), 2.02 (3H, s), 2.03 (3H, s), 2.05 (3H, s), 2.10 (3H, s), 3.45–3.65 (2H, m), 3.76 (3H, s), 3.80–3.90 (1H, m), 4.11 (1H, dd, J=2.2, 12.4 Hz), 4.30 (1H, dd, J=4.0, 12.4 Hz), 5.15–5.35 (3H, m), 5.50–5.60 (1H, m), 6.70–6.85 (2H, m), 7.00–7.10 (2H, m)

Example 30

4-Benzyl-5-methyl-3-(2,3,4,6-tetra-O-acetyl-β-D-glucopyranosyloxy)-1H-pyrazole

The title compound was prepared in a similar manner to that described in Example 15 using 4-benzyl-1,2-dihydro-5-methyl-3H-pyrazol-3-one instead of 1,2-dihydro-4-[(4-isopropoxyphenyl)methyl]-5-methyl-3H-pyrazol-3-one.

¹H-NMR (400 MHz, CDCl₃) δ ppm: 1.86 (3H, s), 2.01 (3H, s), 2.03 (3H, s), 2.06 (3H, s), 2.11 (3H, s), 3.59 (1H, d, J=15.8 Hz), 3.66 (1H, d, J=15.8 Hz), 3.80–3.90 (1H, m), 4.11 (1H, dd, J=2.3, 12.4 Hz), 4.30 (1H, dd, J=4.0, 12.4 Hz), 5.15–5.30 (3H, m), 5.50–5.65 (1H, m), 7.05–7.30 (5H, m), 8.75–9.55 (1H, brs)

Example 31

4-[(4-Methoxyphenyl)methyl]-1.5-dimethyl-3-(2,3,4,6-tetra-O-acetyl-β-D-glucopyranosyloxy)pyrazole A suspension of 4-[(4-methoxyphenyl)methyl]-5-methyl-3-(2,3,4,6-tetra-O-acetyl-β-D-glucopyranosyloxy)-1H-pyrazole (18 mg), potassium carbonate (14 mg) and iodomethane (4.7 mg) in acetonitrile (2 mL) was stirred at 75° C. overnight. The reaction mixture was filtered through celite®, and the solvent of the filtrate was removed under reduced pressure. The residue was purified by preparative thin layer chromatography (developing solvent: benzene/acetone=2/1) to give 4-[(4-methoxyphenyl)methyl]-1,5-dimethyl-3-(2,3,4,6-tetra-O-acetyl-β-D-glucopyranosyloxy)pyrazole (4 mg).

¹H-NMR (500 MHz, CDCl₃) δ ppm: 1.90 (3H, s), 2.01 (3H, s), 2.03 (3H, s), 2.06 (3H, s), 2.07 (3H, s), 3.45–3.60 (2H, m), 3.60 (3H, s), 3.76 (3H, s), 3.80–3.90 (1H, m), 4.13 (1H, dd, J=2.4, 12.4 Hz), 4.29 (1H, dd, J=4.1, 12.4 Hz), 5.15–5.30 (3H, m), 5.50–5.60 (1H, m), 6.70–6.80 (2H, m), 7.00–7.10 (2H, m)

Example 32

1-Methyl-4-[(4-methylthiophenyl)methyl]-3-(2,3,4,6-tetra-O-acetyl-β-D-glucopyranosyloxy)-5-trifluoromethylpyrazole A suspension of 4-[(4-metylthiophenyl)methyl]-3-(2,3,4,6-tetra-O-acetyl-β-D-glucopyranosyloxy)-5-trifluoromethyl-1H-pyrazole (30 mg), potassium carbonate (8.0 mg) and iodomethane (8.2 mg) in tetrahydrofuran (1 mL) was stirred at 75° C. overnight. The reaction mixture was filtered through celite®, and the solvent of the filtrate was removed under reduced pressure. The residue was purified by preparative thin layer chromatography (developing solvent: dichloromethane/ethyl acetate=5/1) to give 1-methyl-4-[(4-methylthiophenyl)methyl]-3-(2,3,4,6-tetra-O-acetyl-β-D-glucopyranosyloxy)-5-trifluoromethylpyrazole (13 mg).

¹H-NMR (500 MHz, CDCl₃) δ ppm: 1.89 (3H, s), 2.02 (3H, s), 2.04 (3H, s), 2.07 (3H, s), 2.44 (3H, s), 3.65–3.95 (6H, m), 4.14 (1H, dd, J=2.3, 12.4 Hz), 4.29 (1H, dd, J=4.3, 12.4 Hz), 5.15–5.35 (3H, m), 5.50–5.65 (1H, m), 7.00–7.20 (4H, m)

Example 33

1-Ethyl-4-[(4-methylthiophenyl)methyl]-3-(2,3,4,6-tetra-O-acetyl-β-D-glucopyranosyloxy)-5-trifluoromethylpyrazole The title compound was prepared in a similar manner to that described in Example 32 using iodoethane instead of iodomethane.

¹H-NMR (500 MHz, CDCl₃) δ ppm: 1.40 (3H, t, J=7.2 Hz), 1.90 (3H, s), 2.02 (3H, s), 2.04 (3H, s), 2.06 (3H, s), 2.44 (3H, s), 3.72 (2H, s), 3.80–3.90 (1H, m), 4.05–4.20 (3H, m), 4.27 (1H, dd, J=4.5, 12.4 Hz), 5.10–5.35 (3H, m), 5.55–5.65 (1H, m), 7.00–7.10 (2H, m), 7.10–7.20 (2H, m)

Example 34

4-[(4-Methylthiophenyl)methyl]-1-propyl-3-(2,3,4,6-tetra-O-acetyl-β-D-glucopyranosyloxy)-5-trifluoromethylpyrazole The title compound was prepared in a similar manner to that described in Example 32 using iodopropane instead of iodomethane.

¹H-NMR (500 MHz, CDCl₃) δ ppm: 0.92 (3H, t, J=7.4 Hz), 1.75–1.90 (2H, m), 1.89 (3H, s), 2.02 (3H, s), 2.04 (3H, s), 2.06 (3H, s), 2.44 (3H, s), 3.72 (2H, s), 3.80–3.90 (1H, m), 3.90–4.05 (2H, m), 4.12 (1H, dd, J=2.3, 12.4 Hz), 4.27 (1H, dd, J=4.5, 12.4 Hz), 5.10–5.35 (3H, m), 5.55–5.65 (1H, m), 7.00–7.10 (2H, m), 7.10–7.20 (2H, m)

Example 35

3-(β-D-Glucopyranosyloxy)-4-[(4-isopropoxyphenyl)methyl]-5-methyl-1H-pyrazole

To a solution of 4-[(4-isopropoxyphenyl)methyl]-5-methyl-3-(2,3,4,6-tetra-O-acetyl-β-D-glucopyranosyloxy)-1H-pyrazole (61 mg) in ethanol (3 mL) was added 1N aqueous sodium hydroxide solution (0.53 mL), and the mixture was stirred at room temperature for 2 hours. The solvent was removed under reduced pressure, and the residue was purified by solid phase extraction on ODS (washing solvent: distilled water, eluent: methanol) to give 3-(β-D-glucopyranosyloxy)-4-[(4-isopropoxyphenyl)methyl]-5-methyl-1H-pyrazole (39 mg).

¹H-NMR (500 MHz, CD₃OD) δ ppm: 1.26 (6H, d, J=5.9 Hz), 2.05 (3H, s), 3.25–3.45 (4H, m), 3.55–3.75 (3H, m), 3.75–3.90 (1H, m), 4.45–4.60 (1H, m), 5.00–5.10 (1H, m), 6.70–6.80 (2H, m), 7.00–7.15 (2H, m)

Example 36

3-(β-D-Glucopyranosyloxy)-5-methyl-4-[(4-propylphenyl)methyl]-1H-pyrazole

The title compound was prepared in a similar manner to that described in Example 35 using 5-methyl-4-[(4-propylphenyl)methyl]-3-(2,3,4,6-tetra-O-acetyl-β-D-glucopyranosyloxy)-1H-pyrazole instead of 4-[(4-isopropoxyphenyl)

methyl]-5-methyl-3-(2,3,4,6-tetra-O-acetyl-β-D-glucopyranosyloxy)-1H-pyrazole.

¹H-NMR (500 MHz, CD₃OD) δ ppm: 0.91 (3H, t, J=7.5 Hz), 1.50–1.65 (2H, m), 2.05 (3H, s), 2.45–2.60 (2H, m), 3.25–3.45 (4H, m), 3.55–3.75 (3H, m), 3.83 (1H, d, J=11.9 Hz), 5.00–5.10 (1H, m), 7.00–7.15 (4H, m)

Example 37

3-(β-D-Glucopyranosyloxy)-4-[(4-isobutylphenyl)methyl]-5-methyl-1H-pyrazole

The title compound was prepared in a similar manner to that described in Example 35 using 4-[(4-isobutylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 0.87 (6H, d, J=6.6 Hz), 1.70–1.90 (1H, m), 2.04 (3H, s), 2.41 (2H, d, J=7.1 Hz), 3.25–3.45 (4H, m), 3.55–3.90 (4H, m), 5.00–5.10 (1H, m), 6.95–7.15 (4H, m)

Example 38

3-(β-D-Glucopyranosyloxy)-5-methyl-4-[(4-propoxyphenyl)methyl]-1H-pyrazole

The title compound was prepared in a similar manner to that described in Example 35 using 5-methyl-4-[(4-propoxyphenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 1.02 (3H, t, J=7.4 Hz), 1.65–1.80 (2H, m), 2.05 (3H, s), 3.25–3.45 (4H, m), 3.60–3.75 (3H, m), 3.80–3.90 (3H, m), 5.00–5.10 (1H, m), 6.70–6.85 (2H, m), 7.05–7.15 (2H, m)

Example 39

4-[(4-Ethoxyphenyl)methyl]-3-(β-D-glucopyranosyloxy)-5-methyl-1H-pyrazole

The title compound was prepared in a similar manner to that described in Example 35 using 4-[(4-ethoxyphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 1.34 (3H, t, J=7.0 Hz), 2.05 (3H, s), 3.25–3.45 (4H, m), 3.60–3.75 (3H, m), 3.80–3.90 (1H, m), 3.97 (2H, q, J=7.0 Hz), 5.00–5.10 (1H, m), 6.70–6.85 (2H, m), 7.05–7.15 (2H, m)

Example 40

3-(β-D-Glucopyranosyloxy)-5-methyl-4-[(4-trifluoromethylphenyl)methyl]-1H-pyrazole The title compound was prepared in a similar manner to that described in Example 35 using 5-methyl-3-(2,3,4,6-tetra-O-acetyl-β-D-glucopyranosyloxy)-4-[(4-trifluoromethylphenyl)methyl]-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 2.08 (3H, s), 3.20–3.40 (4H, m), 3.67 (1H, dd, J=5.0, 11.9 Hz), 3.75–3.90 (3H, m), 5.00–5.10 (1H, m), 7.30–7.45 (2H, m), 7.45–7.60 (2H, m)

Example 41

4-[(4-tert-Butylphenyl)methyl]-3-(β-D-glucopyranosyloxy)-5-methyl-1H-pyrazole

The title compound was prepared in a similar manner to that described in Example 35 using 4-[(4-tert-butylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 1.28 (9H, s), 2.06 (3H, s), 3.25–3.45 (4H, m), 3.60–3.90 (4H, m), 5.00–5.10 (1H, m), 7.05–7.15 (2H, m), 7.20–7.30 (2H, m)

Example 42

4-[(4-Butoxyphenyl)methyl]-3-(β-D-glucopyranosyloxy)-5-methyl-1H-pyrazole

The title compound was prepared in a similar manner to that described in Example 35 using 4-[(4-butoxyphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 0.97 (3H, t, J=7.4 Hz), 1.40–1.55 (2H, m), 1.65–1.80 (2H, m), 2.05 (3H, s), 3.30–3.45 (4H, m), 3.60–3.75 (3H, m), 3.83 (1H, d, J=12.0 Hz), 3.91 (2H, t, J=6.4 Hz), 5.00–5.10 (1H, m), 6.70–6.85 (2H, m), 7.05–7.15 (2H, m)

Example 43

3-(β-D-Glucopyranosyloxy)-5-methyl-4-[(4-methylthiophenyl)methyl]-1H-pyrazole

The title compound was prepared in a similar manner to that described in Example 35 using 5-methyl-4-[(4-methylthiophenyl)methyl]-3-(2,3,4,6-tetra-O-acetyl-β-D-glucopyranosyloxy)-1H-pyrazole instead of 4-[(4-isopropoxyphenyl)methyl] -5-methyl-3-(2,3,4,6-tetra-O-acetyl-β-D-glucopyranosyloxy)-1H-pyrazole.

¹H-NMR (500 MHz, CD₃OD) δ ppm: 2.06 (3H, s), 2.42 (3H, s), 3.20–3.45 (4H, m), 3.55–3.75 (3H, m), 3.80–3.90 (1H, m), 5.00–5.10 (1H, m), 7.05–7.20 (4H, m)

Example 44

5-Ethyl-3-(β-D-glucopyranosyloxy)-4-[(4-methylthiophenyl)methyl]-1H-pyrazole

The title compound was prepared in a similar manner to that described in Example 35 using 5-ethyl-4-[(4-methylthiophenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

¹H-NMR (500 MHz, CD₃OD) δ ppm: 1.06 (3H, t, J=7.6 Hz), 2.42 (3H, s), 2.47 (2H, q, J=7.6 Hz), 3.25–3.45 (4H, m), 3.60–3.80 (3H, m), 3.80–3.90 (1H, m), 5.00–5.10 (1H, m), 7.10–7.20 (4H, m)

Example 45

3-(β-D-Glucopyranosyloxy)-4-[(4-isopropylphenyl)methyl]-5-methyl-1H-pyrazole

The title compound was prepared in a similar manner to that described in Example 35 using 4-[(4-isopropylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 1.20 (6H, d, J=6.9 Hz), 2.05 (3H, s), 2.75–2.90 (1H, m), 3.25–3.45 (4H, m), 3.55–3.90 (4H, m), 5.00–5.10 (1H, m), 7.00–7.15 (4H, m)

Example 46

3-(β-D-Glucopyranosyloxy)-4-[(4-methylthiophenyl)methyl]-5-trifluoromethyl-1H-pyrazole The title compound was prepared in a similar manner to that described in Example 35 using 4-[(4-methylthiophenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 2.42 (3H, s), 3.25–3.50 (4H, m), 3.69 (1H, dd, J=4.9, 12.0 Hz), 3.75–3.90 (3H, m), 4.90–5.10 (1H, m), 7.10–7.20 (4H, m)

Example 47

4-Benzyl-3-(β-D-glucopyranosyloxy)-5-trifluoromethyl-1H-pyrazole

The title compound was prepared in a similar manner to that described in Example 35 using 4-benzyl-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 3.25–3.45 (4H, m), 3.67 (1H, dd, J=5.3, 12.0 Hz), 3.80–3.95 (3H, m), 4.97 (1H, d, J=7.4 Hz), 7.05–7.25 (5H, m)

Example 48

3-(β-D-Glucopyranosyloxy)-4-[(4-methoxyphenyl)methyl]-5-trifluoromethyl-1H-pyrazole The title compound was prepared in a similar manner to that described in Example 35 using 4-[(4-methoxyphenyl)methyl]-3-(2,3,4,6-tetra-O-acetyl-β-D-gluco-pyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 3.25–3.45 (4H, m), 3.67 (1H, d, J=5.4, 12.1 Hz), 3.73 (3H, s), 3.75–3.90 (3H, m), 4.90–5.00 (1H, m), 6.70–6.85 (2H, m), 7.05–7.15 (2H, m)

Example 49

3-(β-D-Glucopyranosyloxy)-4-[(4-methoxyphenyl)methyl]-5-methyl-1H-pyrazole

The title compound was prepared in a similar manner to that described in Example 35 using 4-[(4-methoxyphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 2.04 (3H, s), 3.25–3.45 (4H, m), 3.55–3.75 (3H, m), 3.73 (3H, s), 3.80–3.90 (1H, m), 5.00–5.10 (1H, m), 6.75–6.85 (2H, m), 7.05–7.15 (2H, m)

Example 50

4-Benzyl-3-(β-D-glucopyranosyloxy)-5-methyl-1H-pyrazole

The title compound was prepared in a similar manner to that described in Example 35 using 4-benzyl-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 2.05 (3H, s), 3.25–3.45 (4H, m), 3.60–3.90 (4H, m), 5.00–5.10 (1H, m), 7.05–7.25 (5H, m)

Example 51

3-(β-D-Glucopyranosyloxy)-4-[(4-methoxyphenyl)methyl]-1,5-dimethylpyrazole

The title compound was prepared in a similar manner to that described in Example 35 using 4-[(4-methoxyphenyl)methyl]-1,5-dimethyl-3-(2,3,4,6-tetra-O-acetyl-β-D-glucopyranosyloxy)pyrazole instead of 4-[(4-isopropoxyphenyl)methyl]-5-methyl-3-(2,3,4,6-tetra-O-acetyl-β -D-glucopyranosyloxy)-1H-pyrazole.

$^1$H-NMR (500 MHz, CD$_3$OD) δ ppm: 2.06 (3H, s), 3.25–3.45 (4H, m), 3.55–3.70 (6H, m), 3.73 (3H, s), 3.75–3.90 (1H, m), 5.00–5.10 (1H, m), 6.70–6.80 (2H, m), 7.05–7.15 (2H, m)

Example 52

3-(β-D-Glucopyranosyloxy)-1-methyl-4-[(4-methylthiophenyl)methyl]-5-trifluoromethylpyrazole The title compound was prepared in a similar manner to that described in Example 35 using 1-methyl-4-[(4-methylthiophenyl)methyl]-3-(2,3,4,6-tetra-O-acetyl-β-D-glucopyranosyloxy)-5-trifluoromethylpyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 2.42 (3H, s), 3.30–3.50 (4H, m), 3.69 (1H, dd, J=4.7, 12.0 Hz), 3.75–3.90 (6H, m), 5.25–5.35 (1H, m), 7.05–7.20 (4H, m)

Example 53

1-Ethyl-3-(β-D-glucopyranosyloxy)-4-[(4-methylthiophenyl)methyl]-5-trifluoromethylpyrazole The title compound was prepared in a similar manner to that described in Example 35 using 1-ethyl-4-[(4-methylthiophenyl)methyl]-3-(2,3,4,6-tetra-O-acetyl-β-D-glucopyranosyloxy)-5-trifluoromethylpyrazole instead of 4-[(4-isopropoxyphenyl)methyl]-5-methyl-3-(2,3,4,6-tetra-O-acetyl-β -D-glucopyranosyloxy)-1H-pyrazole.

$^1$H-NMR (500 MHz, CD$_3$OD) δ ppm: 1.38 (3H, t, J=7.1 Hz), 2.42 (3H, s), 3.30–3.50 (4H, m), 3.60–3.75 (1H, m), 3.75–3.90 (1H, m), 4.14 (2H, q, J=7.1 Hz), 5.25–5.35 (1H, m), 7.05–7.20 (4H, m)

Example 54

3-(β-D-Glucopyranosyloxy)-4-[(4-methylthiophenyl)methyl]-1-propyl-5-trifluoromethylpyrazole The title compound was prepared in a similar manner to that described in Example 35 using 4-[(4-methylthiophenyl)methyl]-1-propyl-3-(2,3,4,6-tetra-O-acetyl-β-D-glucopyranosyloxy)-5-trifluoromethylpyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 0.90 (3H, t, J=7.4 Hz), 1.75–1.90 (2H, m), 2.42 (3H, s), 3.30–3.50 (4H, m), 3.69 (1H, dd, J=4.9, 12.0 Hz), 3.75–3.90 (3H, m), 4.00–4.10 (2H, m), 5.25–5.35 (1H, m), 7.05–7.20 (4H, m)

Example 55

3-(β-D-Glucopyranosyloxy)-5-methyl-4-[(4-methylphenyl)methyl]-1H-pyrazole

5-Methyl-4-[(4-methylphenyl)methyl]-3-(2,3,4,6-tetra-O-acetyl-β-D-glucopyranosyloxy)-1H-pyrazole was prepared in a similar manner to that described in Example 15 using 1,2-dihydro-5-methyl-4-[(4-methylphenyl)methyl]-3H-pyrazol-3-one instead of 1,2-dihydro-4-[(4-isopropoxyphenyl)methyl]-5-methyl-3H-pyrazol-3-one. Then, the title compound was prepared in a similar manner to that described in Example 35 using 5-methyl-4-[(4-methylphenyl)methyl]-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 2.04 (3H, s), 2.26 (3H, s), 3.25–3.45 (4H, m), 3.55–3.90 (4H, m), 5.00–5.10 (1H, m), 6.95–7.15 (4H, m)

Example 56

4-[(4-Ethylphenyl)methyl]-3-(β-D-glucopyranosyloxy)-5-methyl-1H-pyrazole

4-[(4-Ethylphenyl)methyl]-5-methyl-3-(2,3,4,6-tetra-O-acetyl-β-D-glucopyranosyloxy)-1H-pyrazole was prepared in a similar manner to that described in Example 15 using 4-[(4-ethylphenyl)methyl]-1,2-dihydro-5-methyl-3H-pyrazol-3-one instead of 1,2-dihydro-4-[(4-isopropoxyphenyl)methyl]-5-methyl-3H-pyrazol-3-one. Then, the title compound was prepared in a similar manner to that described in Example 35 using 4-[(4-ethylphenyl)methyl]-5-methyl-3-(2,3,4,6-tetra-O-acetyl-β-D-glucopyranosyloxy)-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 1.18 (3H, t, J=7.6 Hz), 2.04 (3H, s), 2.57 (2H, q, J=7.6 Hz), 3.25–3.45 (4H, m), 3.55–3.90 (4H, m), 5.00–5.10 (1H, m), 6.95–7.20 (4H, m)

Example 57

3-(β-D-Glucopyranosyloxy)-4-[(4-methylphenyl)methyl]-5-trifluoromethyl-1H-pyrazole 4-[(4-Methylphenyl)methyl]-3-(2,3,4,6-tetra-O-acetyl-β-D-glucopyranosyloxy)-5-trifluoromethyl-1H-pyrazole was prepared in a similar manner to that described in Example 26 using 1,2-dihydro-4-[(4-methylphenyl)methyl]-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Example 35 using 4-[(4-methylphenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 2.25 (3H, s), 3.20–3.45 (4H, m), 3.55–3.70 (1H, m), 3.70–3.90 (3H, m), 4.80–4.95 (1H, m), 6.90–7.15 (4H, m)

Example 58

4-[(4-Ethylphenyl)methyl]-3-(β-D-glucopyranosyloxy)-5-trifluoromethyl-1H-pyrazole 4-[(4-Ethylphenyl)methyl]-3-(2,3,4,6-tetra-O-acetyl-β-D-glucopyranosyloxy)-5-trifluoromethyl-1H-pyrazole was prepared in a similar manner to that described in Example 26 using 4-[(4-ethylphenyl)methyl]-1,2-dihydro-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Example 35 using 4-[(4-ethylphenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 1.18 (3H, t, J=7.6 Hz), 2.50–2.60 (2H, m), 3.15–3.40 (4H, m), 3.55–3.65 (1H, m), 3.70–3.90 (3H, m), 4.80–4.95 (1H, m), 6.95–7.15 (4H, m)

Example 59

3-(β-D-Glucopyranosyloxy)-4-[(4-isopropylphenyl)methyl]-5-trifluoromethyl-1H-pyrazole 4-[(4-Isopropylphenyl)methyl]-3-(2,3,4,6-tetra-O-acetyl-β-D-glucopyranosyloxy)-5-trifluoromethyl-1H-pyrazole was prepared in a similar manner to that described in Example 26 using 1,2-dihydro-4-[(4-isopropylphenyl)methyl]-5-trifluoromethyl-3H-pyrazol-3-one instead of 1,2-dihydro-4-[(4-methylthiophenyl)methyl]-5-trifluoro-methyl-3H-pyrazol-3-one. Then, the title compound was prepared in a similar manner to that described in Example 35 using 4-[(4-isopropylphenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 1.20 (6H, d, J=6.9 Hz), 2.75–2.85 (1H, m), 3.15–3.40 (4H, m), 3.55–3.65 (1H, m), 3.70–3.90 (3H, m), 4.80–4.95 (1H, m), 7.00–7.15 (4H, m)

Example 60

4-[(4-Chlorophenyl)methyl]-3-(β-D-glucopyranosyloxy)-5-trifluoromethyl-1H-pyrazole 4-[(4-Chlorophenyl)methyl]-3-(2,3,4,6-tetra-O-acetyl-β-D-glucopyranosyloxy)-5-trifluoromethyl-1H-pyrazole was prepared in a similar manner to that described in Example 26 using 4-[(4-chlorophenyl)methyl]-1,2-dihydro-5-trifluoromethyl-3H-pyrazol-3-one instead of 1,2-dihydro-4-[(4-methylthiophenyl)methyl]-5-trifluoromethyl-3H-pyrazol-3-one. Then, the title compound was prepared in a similar manner to that described in Example 35 using 4-[(4-chlorophenyl)methyl]-3-(2,3,4,6-tetra-O-acetyl-β-D-glucopyranosyloxy)-5-trifluoromethyl-1H-pyrazole instead of 4-[(4-isopropoxyphenyl)methyl]-5-methyl-3-(2,3,4,6-tetra-O-acetyl-β-D-glucopyranosyloxy)-1H-pyrazole.

$^1$H-NMR (500 MHz, CD$_3$OD) δ ppm: 3.20–3.40 (4H, m), 3.55–3.70 (1H, m), 3.75–3.90 (3H, m), 4.80–4.95 (1H, m), 7.10–7.25 (4H, m)

Example 61

3-(β-D-Glucopyranosyloxy)-4-[(4-isopropoxyphenyl)methyl]-5-methyl-1-propylpyrazole To a suspension of 3-(β-D-glucopyranosyloxy)-4-[(4-isopropoxyphenyl)methyl]-5-methyl-1H-pyrazole (50 mg) and cesium carbonate (0.20 g) in N,N-dimethylformamide (1 mL) was added iodopropane (0.036 mL) at 50° C., and the mixture was stirred overnight. Water was added to the reaction mixture, and the resulting mixture was purified by solid phase extraction on ODS (washing solvent:distilled water, eluent:methanol). The resulting semi-purified material was purified by column chromatography on silica gel (eluent: dichloromethane/methanol=8/1) to give 3-(β-D-glucopyranosyloxy)-4-[(4-isopropoxyphenyl)methyl]-5-methyl-1-propylpyrazole (28 mg).

$^1$H-NMR (500 MHz, CD$_3$OD) δ ppm: 0.87 (3H, t, J=7.4 Hz), 1.26 (6H, d, J=6.0 Hz), 1.65–1.80 (2H, m), 2.07 (3H, s), 3.25–3.45 (4H, m), 3.55–3.75 (3H, m), 3.75–3.95 (3H, m), 4.40–4.60 (1H, m), 5.00–5.10 (1H, m), 6.70–6.80 (2H, m), 7.00–7.10 (2H, m)

Example 62

1-Ethyl-3-(β-D-glucopyranosyloxy)-4-[(4-isopropylphenyl)methyl]-5-methylpyrazole The title compound was prepared in a similar manner to that described in Example 61 using iodoethane instead of iodpropane.

$^1$H-NMR (500 MHz, CD$_3$OD) δ ppm: 1.26 (6H, d, J=6.0 Hz), 1.29 (3H, t, J=7.2 Hz), 2.08 (3H, s), 3.25–3.45 (4H, m), 3.55–3.75 (3H, m), 3.75–3.90 (1H, m), 3.96 (2H, q, J=7.2 Hz), 4.40–4.60 (1H, m), 5.00–5.10 (1H, m), 6.70–6.80 (2H, m), 7.00–7.10 (2H, m)

Example 63

1-Ethyl-3-(β-D-glucopyranosyloxy)-4-[(4-methoxyphenyl)methyl]-5-methylpyrazole

The title compound was prepared in a similar manner to that described in Example 61 using 3-(β-D-glucopyranosyloxy)-4-[(4-methoxyphenyl)methyl]-5-methyl-1H-pyrazole instead of 3-(β-D-glucopyranosyloxy)-4-[(4-isopropoxyphenyl)methyl]-5-methyl-1H-pyrazole and using iodoethane instead of iodopropane.

$^1$H-NMR (500 MHz, CD$_3$OD) δ ppm: 1.29 (3H, t, J=7.1 Hz), 2.07 (3H, s), 3.20–3.45 (4H, m), 3.55–3.75 (6H, m), 3.82 (1H, dd, J=2.0, 12.0 Hz), 3.90–4.05 (2H, m), 5.00–5.10 (1H, m), 6.70–6.85 (2H, m), 7.05–7.15 (2H, m)

Example 64

3-(β-D-Glucopyranosyloxy)-4-[(4-methoxyphenyl)methyl]-5-methyl-1-propylpyrazole

The title compound was prepared in a similar manner to that described in Example 61 using 3-(β-D-glucopyranosyloxy)-4-[(4-methoxyphenyl)methyl]-5-methyl-1H-pyrazole instead of 3-(β-D-glucopyranosyloxy)-4-[(4-isopropoxyphenyl)methyl]-5-methyl-1H-pyrazole.

$^1$H-NMR (500 MHz, CD$_3$OD) δ ppm: 0.87 (3H, t, J=7.5 Hz), 1.65–1.80 (2H, m), 2.07 (3H, s), 3.35–3.45 (4H, m), 3.60–3.75 (3H, m), 3.73 (3H, s), 3.75–3.85 (1H, m), 3.85–3.95 (2H, m), 5.00–5.10 (1H, m), 6.70–6.85 (2H, m), 7.00–7.15 (2H, m)

Example 65

1-Ethyl-4-[(4-ethoxyphenyl)methyl]-3-(β-D-glucopyranosyloxy)-5-methylpyrazole

The title compound was prepared in a similar manner to that described in Example 61 using 4-[(4-ethoxyphenyl)methyl]-5-methyl-3-(β-D-glucopyranosyloxy)-1H-pyrazole instead of 3-(β-D-glucopyranosyloxy)-4-[(4-isopropoxyphenyl)methyl]-5-methyl-1H-pyrazole and using iodoethane instead of iodopropane.

$^1$H-NMR (500 MHz, CD$_3$OD) δ ppm: 1.28 (3H, t, J=7.4 Hz), 1.34 (3H, t, J=7.2 Hz), 2.07 (3H, s), 3.25–3.45 (4H, m), 3.55–3.75 (3H, m), 3.75–3.85 (1H, m), 3.90–4.00 (4H, m), 5.00–5.10 (1H, m), 6.70–6.85 (2H, m), 7.00–7.15 (2H, m)

Example 66

4-[(4-Ethoxyphenyl)methyl]-3-(β-D-glucopyranosyloxy)-5-methyl-1-propylpyrazole

The title compound was prepared in a similar manner to that described in Example 61 using 4-[(4-ethoxyphenyl)methyl]-5-methyl-3-(β-D-glucopyranosyloxy)-1H-pyrazole instead of 3-(β-D-glucopyranosyloxy)-4-[(4-isopropoxyphenyl)methyl]-5-methyl-1H-pyrazole.

$^1$H-NMR (500 MHz, CD$_3$OD) δ ppm: 0.87 (3H, t, J=7.6 Hz), 1.34 (3H, t, J=7.1 Hz), 1.65–1.80 (2H, m), 2.07 (3H, s), 3.25–3.45 (4H, m), 3.55–3.75 (3H, m), 3.81 (1H, dd, J=2.1, 12.1 Hz), 3.85–4.05 (4H, m), 5.00–5.10 (1H, m), 6.70–6.85 (2H, m), 7.00–7.15 (2H, m)

Example 67

1-Ethyl-4-[(4-ethylphenyl)methyl]-3-(β-D-glucopyranosyloxy)-5-methylpyrazole

The title compound was prepared in a similar manner to that described in Example 61 using 4-[(4-ethylphenyl)methyl]-5-methyl-3-(β-D-glucopyranosyloxy)-1H-pyrazole instead of 3-(β-D-glucopyranosyloxy)-4-[(4-isopropoxyphenyl)methyl]-5-methyl-1H-pyrazole and using iodoethane instead of iodopropane.

¹H-NMR (500 MHz, CD₃OD) δ ppm: 1.17 (3H, t, J=7.6 Hz), 1.28 (3H, t, J=7.2 Hz), 2.06 (3H, s), 2.56 (2H, q, J=7.6 Hz), 3.25–3.45 (4H, m), 3.55–3.75 (3H, m), 3.75–3.85 (1H, m), 3.90–4.00 (2H, m), 5.00–5.10 (1H, m), 7.00–7.15 (4H, m)

Example 68

4-[(4-Ethylphenyl)methyl]-3-(β-D-glucopyranosyloxy)-5-methyl-1-propylpyrazole

The title compound was prepared in a similar manner to that described in Example 61 using 4-[(4-ethylphenyl)methyl]-5-methyl-3-(β-D-glucopyranosyloxy)-1H-pyrazole instead of 3-(β-D-glucopyranosyloxy)-4-[(4-isopropoxy-henyl)methyl]-5-methyl-1H-pyrazole.

$^1$H-NMR (500 MHz, CD$_3$OD) δ ppm: 0.87 (3H, t, J=7.4 Hz), 1.17 (3H, t, J=7.6 Hz), 1.65–1.80 (2H, m), 2.06 (3H, s), 2.56 (2H, q, J=7.6 Hz), 3.25–3.45 (4H, m), 3.60–3.95 (6H, m), 5.00–5.10 (1H, m), 7.00–7.15 (4H, m)

Example 69

1-Butyl-3-(β-D-glucopyranosyloxy)-4-[(4-isopropoxyphenyl)methyl]-5-methylpyrazole The title compound was prepared in a similar manner to that described in Example 61 using bromobutane instead of iodpropane.

$^1$H-NMR (500 MHz, CD$_3$OD) δ ppm: 0.92 (3H, t, J=7.4 Hz), 1.20–1.40 (8H, m), 1.60–1.75 (2H, m), 2.07 (3H, s), 3.25–3.45 (4H, m), 3.55–3.75 (3H, m), 3.81 (1H, dd, J=2.1, 12.0 Hz), 3.91 (2H, t, J=7.2 Hz), 4.45–4.55 (1H, m), 5.00–5.10 (1H, m), 6.70–6.80 (2H, m), 7.00–7.10 (2H, m)

Example 70

3-(β-D-Glucopyranosyloxy)-4-[(4-isopropoxyphenyl)methyl]-1-isopropyl-5-methylpyrazole The title compound was prepared in a similar manner to that described in Example 61 using 2-bromopropane instead of iodopropane.

$^1$H-NMR (500 MHz, CD$_3$OD) δ ppm: 1.26 (6H, d, J=6.0 Hz), 1.30–1.40 (6H, m), 2.08 (3H, s), 3.15–3.45 (4H, m), 3.55–3.75 (3H, m), 3.78 (1H, dd, J=2.3, 12.0 Hz), 4.35–4.45 (1H, m), 4.45–4.55 (1H, m), 5.00–5.10 (1H, m), 6.70–6.80 (2H, m), 7.00–7.10 (2H, m)

Test Example 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using Super Script preamplification system (Gibco-BRL: LIFE TECHNOLOGIES). The DNA fragment coding for human SGLT2 was amplified by the PCR reaction, in which the human kidney cDNA library described above was used as the template and the following oligo nucleotides 0702F and 0712R, presented as sequence number 1 and 2 respectively, were used as the primers. The amplified DNA fragment was ligated into pCR (Invitrogen), a vector for cloning, according to standard method of the kit. The Escherichia coli HB101 was transformed according to usual method and then selection of the transformants was performed on the LB agar medium containing 50 μg/mL of kanamycin. After plasmid DNA was extracted and purified from the one of the transformants, amplifying of the DNA fragment coding for human SGLT2 was performed by the PCR reaction, in which the following oligo nucleotides 0714F and 0715R, presented as sequence number 3 and 4 respectively, were used as the primers. The amplified DNA fragment was digested with restriction enzymes, Xho I and Hind III, and then purified with Wizard purification System (Promega). This purified DNA fragment was inserted at into the corresponding restriction sites of pcDNA3.1 (–) Myc/His-B (Invitrogen), a vector for expressing of fusion protein. The Escherichia coli HB101 was transformed according to usual method and then selection of the transformant was performed on the LB agar medium containing 50 μg/mL of ampicillin. After plasmid DNA was extracted and purified from this transformant, the base sequence of the DNA fragment inserted at the multi-cloning sites of the vector pcDNA3.1 (–) Myc/His-B was analyzed. This clone had a single base substitution (ATC which codes for the isoleucine-433 was substituted by GTC) compared with the human SGLT2 reported by Wells et al (Am. J. Physiol., Vol. 263, pp. 459–465 (1992)). Sequentially, a clone in which valine is substituted for isoleucine-433 was obtained. This plasmid vector expressing human SGLT2 in which the peptide presented as sequence number 5 is fused to the carboxyl terminal alanine residue was designated KL29.

```
Sequence Number 1    ATGGAGGAGCACACAGAGGC

Sequence Number 2    GGCATAGAAGCCCCAGAGGA

Sequence Number 3    AACCTCGAGATGGAGGAGCACACAGAGGC

Sequence Number 4    AACAAGCTTGGCATAGAAGCCCCAGAGGA

Sequence Number 5    KLGPEQKLISEEDLNSAVDHHHHHH
```

2) Preparation of the Cells Expressing Transiently Human SGLT2

KL29, the plasmid expressing human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 μF, 2×10$^6$ cells of COS-7 cell and 20 μg of KL29 in 500 μL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 μL of this cell suspension was added. After overnight culture at 37° C. under 5% CO$_2$, 125 μL of DMEM medium which is containing 10% of fetal bovine serum (Sanko Jyunyaku), 100 units/mL sodium penicillin G (Gibco-BRL: LIFE TECHNOLOGIES), 100 μg/mL streptomycin sulfate (Gibco-BRL: LIFE TECHNOLOGIES) was added to each well. These cells were cultured until the next day and then they were used for the measurement of the inhibitory activity against the uptake of methyl-α-D-glucopyranoside.

3) Measurement of the Inhibitory Activity Against the Uptake of methyl-α-D-glucopyranoside After a test compounds was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris(hydroxymethyl)aminomethane), each diluent was used as test sample for measurement of the inhibitory activity. After removal of the medium of the COS-7 cells expressing transiently human SGLT2, to each well 200 μL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)aminomethane) was added, and the cells were incubated at 37° C. for 10 minutes. After the pretreatment buffer was removed, 200 μL of the same buffer was added again, and the cells were incubated at 37° C. for 10 minutes. The buffer for measurement was prepared by adding of 7 μL of methyl-α-D-(U-14C) glucopyranoside (Amersham Pharmacia Biotech) to 525 μL of the prepared test sample. For the control, the buffer for measurement without test compound was prepared. For estimate of the basal uptake in the absence of test compound and sodium, the buffer for measurement of the basal uptake, which contains 140 mM choline chloride in place of sodium chloride, was prepared similarly. After the pretreatment buffer was removed, 75 μL of the each buffer for measurement was added to each well, the cells were incubated at 37° C. for 2 hours. After the buffer for measurement was removed, 200 μL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris(hydroxymethyl)aminomethane)was added to each well and immediately removed. After two additional washing, the cells were solubilized by addition of 75 μL of 0.2 N sodium hydroxide to each well. After the cell lysates were transferred to the PicoPlate (Packard) and 150 μL of MicroScint-40 (Packard) was added to each well, the radioactivity was measured with microplate scintillation counter TopCount (Packard). The difference in uptake was obtained as 100% value by subtracting the radioactivity in the basal uptake from that in control and then the concentrations at which 50% of uptake were inhibited (IC$_{50}$) were calculated from the concentration-inhibition curve by least square method. The results are shown in the following Table 1.

TABLE 1

| Test compound | IC$_{50}$ value (nM) |
|---|---|
| Example 35 | 181 |
| Example 36 | 441 |
| Example 37 | 346 |
| Example 38 | 702 |
| Example 39 | 185 |
| Example 43 | 84 |
| Example 44 | 509 |
| Example 45 | 441 |
| Example 46 | 679 |
| Example 48 | 415 |
| Example 49 | 383 |
| Example 52 | 835 |
| Example 55 | 280 |
| Example 56 | 190 |
| Example 58 | 634 |
| WAY-123783 | >100000 |

Test Example 2

Assay for the Facilitatory Effect on Urinary Glucose Excretion

Method A)

As experimental animal, overnight fasted SD rats (SLC, male, 5 weeks of age, 120–150 g) were used. Test compound (25.40 mg) was suspended in 762 μL of ethanol and dissolved by adding of 3.048 mL of polyethylene glycol 400 and 3.81 mL of saline and then 3.3 mg/mL solution was prepared. A part of this solution was diluted with the solvent (saline:polyethylene glycol 400:ethanol=5:4:1) and then each solution at the concentration of 3.3, 1 or 0.33 (mg/mL) was prepared. Each of these solutions was subcutaneously administrated to the rats at the dose of 3 mL/kg (10, 3 and 1 mg/kg). For the control, just only the solvent (saline:polyethylene glycol 400:ethanol=5:4:1) was subcutaneously administrated at the dose of 3 mL/kg. Immediately after this subcutaneous administration, 200 g/L glucose solution was orally administered at the dose of 10 mL/kg (2 g/kg). The subcutaneous administration was performed with 26G needle and 1 mL syringe. The oral administration was performed with gastric tube for rat and 2.5 mL syringe. The head count in one group was 3. Collection of urine was performed in metabolic cage after these administrations were finished. The sampling time for collection of urine was 4 hours after the glucose administration. After collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion in 4 hours per 1 body was calculated from urine volume and urinary glucose concentration.

Method B)

As experimental animal, overnight fasted SD rats (SLC, male, 7 weeks of age, 180–220 g) were used. A test compound (10 mg) was suspended or dissolved in 300 μL of ethanol and dissolved by adding of 1.2 mL of polyethylene glycol 400 and 1.5 mL of saline and then 3.3 mg/mL solution was prepared. A part of this solution was diluted with the solvent (saline:polyethylene glycol 400:ethanol=5:4:1) and then each solution at the concentration of 3.3, 0.33 or 0.033 (mg/mL) was prepared. After the body weights of the rats were measured, the test compound solution was administrated by intravenous injection to the tail vein at the dose of 3 mL/kg (10, 1 and 0.1 mg/kg). For the control, just only the solvent (saline:polyethylene glycol 400:ethanol=5:4:1) was administrated by intravenous injection to the tail vein at the dose of 3 mL/kg. Immediately after this intravenous administration, 200 g/L glucose solution was orally administered at the dose of 10 mL/kg (2 g/kg). The intravenous administration was performed with 26G needle and 1 mL syringe. The oral administration was performed with gastric tube for rat and 2.5 mL syringe. The head count in one group was 3. Collection of urine was performed in metabolic cage after the glucose administration was finished. The sampling time for collection of urine was 24 hours after the glucose administration. After collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion in 24 hours per 200 g of body weight was calculated from urine volume, urinary glucose concentration and body weight.

The results are shown in the following Table 2.

TABLE 2

| Test compound | Method | Dose (mg/kg) | Amount of Urinary Glucose Excretion (mg) |
|---|---|---|---|
| Example 35 | B | 0.1 | 16 |
|  |  | 1 | 74 |
|  |  | 10 | 188 |
| Example 45 | A | 1 | 22.1 |
|  |  | 3 | 83.2 |
|  |  | 10 | 153.3 |
|  | B | 0.1 | 2 |
|  |  | 1 | 45 |
|  |  | 10 | 132 |

Test Example 3

Acute Toxicity Test

Method A)

By adding of 0.5% sodium carboxymethylcellulose solution to the test compound, 100 mg/mL suspension was prepared. As experimental animal, male 6–7 weeks of age ICR mice fasted for 4 hours (Clea Japan, 28–33 g, 5 animals in each group) were used. The test suspension described above was orally administered to the experimental animals described above at the dose of 10 mL/kg (1000 mg/kg) and then observation was performed until 24 hours after the administration.

Method B)

By adding of the solvent (saline:polyethylene glycol 400:ethanol=5:4:1) to the test compound, 200 mg/mL suspension was prepared. As experimental animal, male 5 weeks of age ICR mice fasted for 4 hours (Clea Japan, 26–33 g, 5 animals in each group) were used. The test suspension described above was subcutaneously administered to the experimental animals described above at the dose of 3 mL/kg (600 mg/kg) and then observation was performed until 24 hours after the administration.

The results are shown in the following Table 3.

TABLE 3

| Test compound | Method | Death number |
|---|---|---|
| Example 35 | B | 0/5 |
| Example 45 | A | 0/5 |

INDUSTRIAL APPLICABILITY

The glucopyranosyloxybenzylbenzene derivatives represented by the above general formula (I) of the present invention and pharmaceutically acceptable salts thereof have an inhibitory activity in human SGLT2 and exert an excellent hypoglycemic effect by excreting excess glucose in the urine through preventing the reabsorption of glucose at the kidney. Therefore, agents for the prevention or treatment of diabetes, diabetic complications, obesity or the like can be provided by comprising the glucopyranosyloxybenzylbenzene derivative represented by the above general formula (I) of the present invention or pharmaceutically acceptable salt thereof.

In addition, the compounds represented by the above general formulae (V) and (VII), and salts thereof are important as intermediates in the production of the compounds represented by the above general formula (I) and pharmaceutically acceptable salts thereof. Accordingly, the compounds represented by the above general formula (I) of the present invention and pharmaceutically acceptable salts thereof can be readily prepared via these compounds.

The invention claimed is:

1. A glucopyranosyloxypyrazole derivative, wherein the derivative is 3-(β-D-glucopyranosyloxy)-4-[(4-isopropoxyphenyl)methyl]-1-isopropyl-5-methylpyrazole or a pharmaceutically acceptable salt thereof.

* * * * *